United States Patent [19]

Maurer

[11] Patent Number: 4,658,025
[45] Date of Patent: Apr. 14, 1987

[54] HYDRAZINE-THIOCARBOXYLIC ACID O-CARBAMOYLMETHYL ESTERS

[75] Inventor: Fritz Maurer, Wuppertal, Fed. Rep. of Germany

[73] Assignee: Bayer Aktiengesellschaft, Leverkusen, Fed. Rep. of Germany

[21] Appl. No.: 684,568

[22] Filed: Dec. 21, 1984

[30] Foreign Application Priority Data

Jan. 4, 1984 [DE] Fed. Rep. of Germany ....... 3400170

[51] Int. Cl.$^4$ ................. C07C 155/02; C07D 211/06; C07D 223/04; C07D 215/08
[52] U.S. Cl. .................................... 540/607; 544/160; 544/386; 546/19; 546/164; 546/165; 548/540; 558/233
[58] Field of Search ............... 548/142, 540; 564/220, 564/219; 260/455 A; 71/90; 558/233; 544/160, 386; 546/245, 164, 165, 19; 540/607

[56] References Cited

U.S. PATENT DOCUMENTS

| | | | |
|---|---|---|---|
| 3,089,887 | 5/1963 | Metivier | 260/455 A |
| 3,261,858 | 7/1966 | D'Amico | 260/455 A |
| 3,395,234 | 7/1968 | Hopkins et al. | 260/455 A |
| 3,562,284 | 2/1971 | Newmann et al. | 260/455 A |
| 4,384,881 | 5/1983 | Kuyama et al. | 71/90 |
| 4,465,504 | 8/1984 | Forster et al. | 71/90 |
| 4,581,175 | 4/1986 | Maurer | 558/233 |

FOREIGN PATENT DOCUMENTS

| | | | |
|---|---|---|---|
| 0029171 | 5/1981 | European Pat. Off. | 548/142 |
| 2914003 | 10/1980 | Fed. Rep. of Germany | 71/90 |

OTHER PUBLICATIONS

Sandstrom, Svensk Kem. Tidskr. 68:3 pp. 131–154, Studies on Dithiocarbhydrazides (1956).
Sasse, Liebigs Ann. Chem. 735 pp. 158–188, Struktur der Reaktionsprodukte Thio Semicarbaziden und Reacktiuen Kohlensaure (1970).
J. Org. Chem. 11, 1946, pp. 741 and 746.
Methoden Der Organischen Chemie, vol. 111, 1952 p. 680.
J. Chem. Soc., 1950 pp. 3389, 3392, 197 and 290.

Primary Examiner—Glennon H. Hollrah
Assistant Examiner—D. Dinner
Attorney, Agent, or Firm—Sprung Horn Kramer & Woods

[57] ABSTRACT

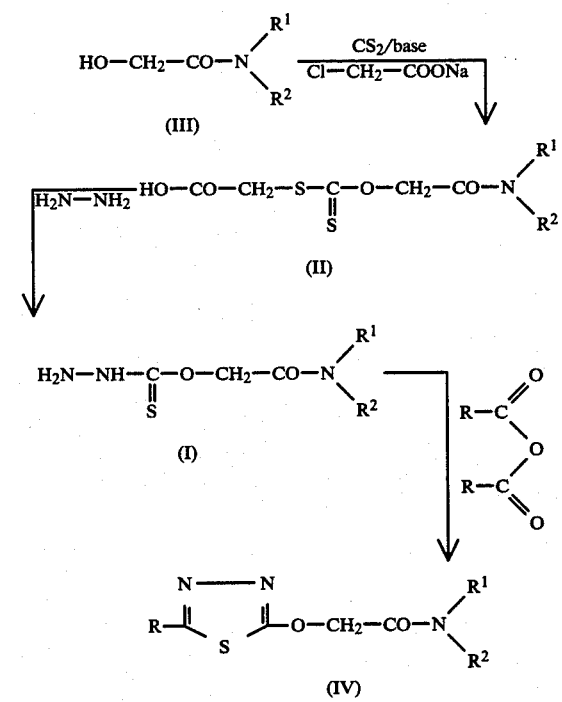

(IV) is a known herbicide while (II) and (I) are new intermediates therefor.

2 Claims, No Drawings

HYDRAZINE-THIOCARBOXYLIC ACID O-CARBAMOYLMETHYL ESTERS

The invention relates to new hydrazine-thiocarboxylic acid O-carbamoylmethyl esters, several processes for their preparation and their use as intermediates for the synthesis of 1,3,4-thiadiazol-2-yloxyacetamides, which have herbicidal properties.

It is already known that herbicidal heteroaryloxyacetamides are obtained if 2-halogeno-heteroaromatics are reacted with hydroxyacetamides (compare, for example, DE-OS (German Published Specification) No. 2,914,003 and DE-OS No. 3,004,326 [=European Pat. No. 18,497], DE-OS No. 2,946,526 [=European Pat. No. 29,171] and (Application Ser. No. 490,900 filed May 2, 1983, now pending Corresponding to German No. 3,218,482).

However, especially in the case of the 1,3,4-thiadiazol-2-yloxyacetamides, the desired herbicidal end products are not obtained in a satisfactory yield or purity when 2-halogeno-1,3,4-thiadiazoles are used as the starting substances.

New hydrazine-thiocarboxylic acid O-carbamoylmethyl esters of the general formula (I)

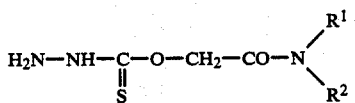

in which
R¹ and R² independently of one another represent hydrogen, alkyl, alkenyl, alkinyl, in each case optionally substituted cycloalkyl or cycloalkenyl, halogenoalkyl, alkoxyalkyl, alkoxy, aralkyl or optionally substituted aryl or
R¹ and R², together with the nitrogen atom to which they are bonded, represent an optionally substituted, saturated or unsaturated heterocyclic radical, which can contain further hetero-atoms,
have been found.

It has furthermore been found that the new hydrazine-thiocarboxylic acid O-carbamoylmethyl esters of the general formula (I)

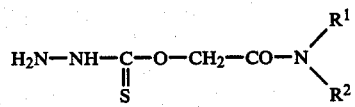

in which
R¹ and R² independently of one another represent hydrogen, alkyl, alkenyl, alkinyl, in each case optionally substituted cycloalkyl or cycloalkenyl, halogenoalkyl, alkoxyalkyl, alkoxy, aralkyl or optionally substituted aryl or
R¹ and R², together with the nitrogen atom to which they are bonded, represent an optionally substituted, saturated or unsaturated heterocyclic radical, which can contain further hetero-atoms,
are obtained by a process in which
(a) O-carbamoylmethyl S-carboxymethyl dithiocarbonates of the general formula (II),

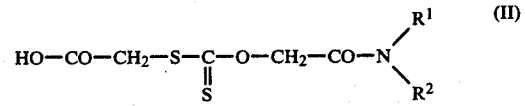

in which
R¹ and R² have the abovementioned meanings,
are reacted with hydrazine hydrate, if appropriate in the presence of a diluent and if appropriate in the presence of an acid-binding agent, or in which
(b) hydroxyacetamides of the general formula (III)

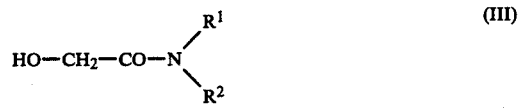

in which
R¹ and R² have the abovementioned meanings,
are reacted successively in a "one-pot process", first with carbon disulphide in the presence of a base, and then with an alkali metal chloroacetate, and finally with hydrazine hydrate, if appropriate in the presence of a diluent.

Finally, it has been found that the new hydrazinethiocarboxylic acid O-carbamoylmethyl esters of the formula (I) are useful intermediates for the preparation of plant protection agents which have herbicidal properties.

Surprisingly, 1,3,4-thiadiazol-2-yloxyacetamides are obtained in considerably better yields and higher purity when the new hydrazine-thiocarboxylic acid O-carbamoylmethyl esters of the formula (I) are used as the starting substances than when the 2-halogeno-1,3,4-thiadiazoles known from the prior art are used as starting substances.

Formula (I) provides a general definition of the hydrazine-thiocarboxylic acid O-carbamoylmethyl esters according to the invention.

Preferred compounds of the formula (I) are those in which
R¹ amd R² independently of one another represent hydrogen, straight-chain or branched alkyl with 1 to 8 carbon atoms, straight-chain or branched alkenyl or alkinyl with in each case 2 to 8 carbon atoms, cycloalkyl or cycloalkenyl, each of which has 3 to 7 carbon atoms and each of which is optionally mono- or poly-substituted by identical or different substituents, possible substituents being, in particular, alkyl radicals with 1 to 4 carbon atoms, straight-chain or branched alkoxy or alkoxyalkyl with 1 to 8 carbon atoms, halogenoalkyl with 1 to 8 carbon atoms and 1 to 5 halogen atoms, in particular fluorine, chlorine and bromine, aralkyl with 6 to 10 carbon atoms in the aryl part and 1 or 2 carbon atoms in the alkyl part, or aryl which has 6 to 10 carbon atoms and is optionally mono- or poly-substituted by identical or different substituents, possible substituents being: halogen, straight-chain or branched alkyl, alkoxy or alkylthio with in each case 1 to 4 carbon atoms, halogenoalkyl, halogenoalkoxy or halogenoalkylthio with in each case 1 or 2 carbon atoms and 1 to 5 halogen atoms, in particular fluorine, chlorine or bromine, and nitro, or $R^1$ and $R^2$, together with the nitrogen atom to which they are bonded, represent a saturated or unsaturated 5-membered to 7-membered heterocyclic radical which is optionally mono- or poly-substituted by identical or different substituents and which can contain up to 2 further hetero-atoms, in particular nitrogen and oxygen, possible substituents being: straight-chain or branched alkyl with 1 to 6 carbon atoms, also in the form of a fused-on ring system, aryl with 6 to 10 carbon atoms, also in the form of a fused-on ring system, and dioxyalkylene with 2 or 3 carbon atoms.

Particularly preferred hydrazine-thiocarboxylic acid O-carbamoylmethyl esters of the formula (I) are those in which $R^1$ and $R^2$ independently of one another represent hydrogen, straight-chain or branched alkyl with 1 to 6 carbon atoms, straight-chain or branched alkenyl or alkinyl with in each case 2 to 6 carbon atoms, cycloalkyl or cycloalkenyl each of which has 5 to 7 carbon atoms and is optionally mono-, di- or tri-substituted by identical or different substituents from the group comprising methyl and ethyl, branched or straight-chain alkoxy or alkoxyalkyl with 1 to 6 carbon atoms, halogenoalkyl with 1 to 6 carbon atoms and 1 to 5 halogen atoms, in particular fluorine, bromine and chlorine, benzyl, or phenyl which is optionally mono-, di- or tri-substituted by identical or different substituents, particularly preferred substituents being: methyl, ethyl, methoxy, methylthio, trifluoromethyl, trifluoromethoxy, trifluoromethylthio, fluoro, chloro and nitro, or $R^1$ and $R^2$, together with the nitrogen atom to which they are bonded, represent one of the following heterocyclic radicals, optionally mono-, di- or tri-substituted by identical or different substituents:

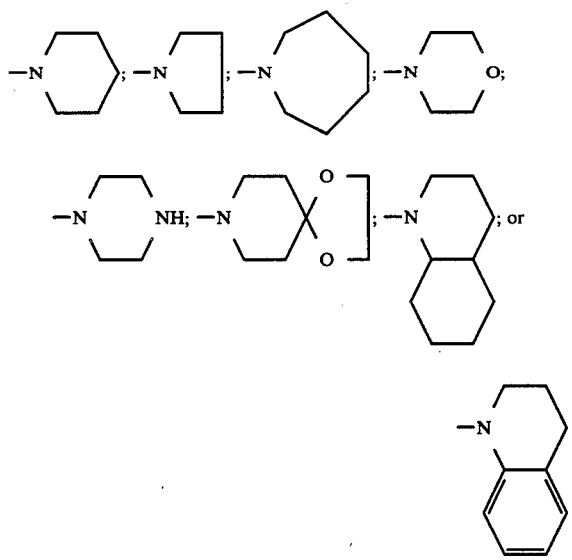

particularly preferred substituents being: methyl, ethyl and phenyl.

The following compounds of the general formula (I) may be mentioned specifically, in addition to the compounds mentioned in the preparation examples:

TABLE 1

$$H_2N-NH-CS-O-CH_2-CO-N\begin{matrix}R^1\\R^2\end{matrix} \quad (I)$$

| $R^1$ | $R^2$ | $R^1$ | $R^2$ |
|---|---|---|---|
| $C_2H_5$ | $C_6H_5$ | $CH_3$ | $-CH\begin{matrix}CH_3\\C_2H_5\end{matrix}$ |
| $C_2H_5$<br>$CH_2=CH-CH_2-$<br>$-CH_2-CH_2-CH_2-CH_2-CH_2-$ | $C_2H_5$<br>$CH_2=CH-CH_2-$ | $CH_3$<br>$-CH_2-C\equiv CH$ | $-CH_2-C\equiv CH$<br>$-CH_2-C\equiv CH$ |
| $CH_3$ | (3-methylphenyl) | $CH_3$ | $-CH\begin{matrix}CH_3\\CH=CH_2\end{matrix}$ |
| $CH_3$ | $-CH\begin{matrix}CH_3\\C\equiv CH\end{matrix}$ | $C_2H_5$ | $-CH(CH_3)_2$ |
| $CH_3O-CH_2-CH_2-$ | $CH_3O-CH_2-CH_2-$ | $-CH_2-CH_2-CH_2-$(cyclohexyl, H) | |

TABLE 1-continued $$H_2N-NH-CS-O-CH_2-CO-N\begin{matrix}R^1\\R^2\end{matrix} \qquad (I)$$

| $R^1$ | $R^2$ | $R^1$ | $R^2$ |
|---|---|---|---|
| CH₃ | CH₃ 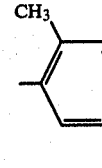 NO₂ | \-CH-CH₂-CH-CH₂-CH- <br> ｜ ｜ ｜ <br> CH₃ CH₃ CH₃ | |
| -CH₂-CH₂-CH₂-CH₂-CH- <br> ｜ <br> CH₃ | | -CH₂-CH-CH₂-CH₂-CH₂- <br> ｜ <br> CH₃ | |
| -CH₂-CH₂-CH-CH₂-CH₂- <br> ｜ <br> CH₃ | | -CH₂-CH-CH₂-CH₂-CH₂- <br> ｜ <br> C₂H₅ | |
| -CH₂-CH₂-CH₂-CH₂- | | | |
| -CH₂-CH₂-CH₂-CH₂-CH₂-CH₂- | CH₃ | 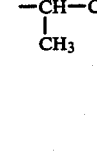 CH₃ | |
| -CH₂-CH₂-CH₂ 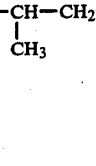 | | -CH₂-CH-CH₂-CH-CH₂- <br> ｜ ｜ <br> CH₃ CH₃ | |
| -CH₂-CH₂-O-CH₂-CH₂- | | | |
| -CH₂-CH₂-NH-CH₂-CH₂- | C₂H₅ | 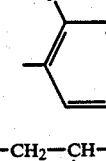 CH₃ | |
| -CH₂-CH₂-N-CH₂-CH₂- <br> ｜ <br> C₆H₅ | CH₃ | 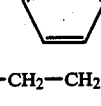 Cl | |
| -CH₂-CH₂-CH-CH₂-CH- <br> ｜ ｜ <br> CH₃ CH₃ | CH₃ | -(CH₂)₃-CH₃ | |
| CH₃ | 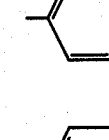 CF₃ | OCH₃ | -CH\<CH₃ <br>   C₂H₅ |
| -CH₂-CH₂-CH-CH₂-CH₂- <br> ｜ <br> C₂H₅ | | CH₃ | 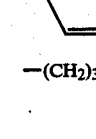 NO₂ |
| CH₃ | -CH₂-C₆H₅ | CH₃ | 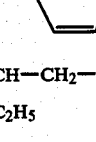 Cl Cl |

TABLE 1-continued $$H_2N-NH-CS-O-CH_2-CO-N\begin{matrix}R^1\\R^2\end{matrix} \quad (I)$$

| R¹ | R² | R¹ | R² |
|---|---|---|---|
| $CH_3$ | 2-methyl-6-chlorophenyl | $CH_3-(CH_2)_3-$ | $CH_3-(CH_2)_3-$ |
| $CH_3$ | 4-chlorophenyl | $CH_3$ | $-CH_2OCH_3$ |
|  |  | $C_2H_5$ | $-CH_2-CF_3$ |
| $CH_3$ | 2,3-dichlorophenyl | $(CH_3)_2CH-$ | $C_6H_5$ |

If, for example, S-carboxymethyl O-(N-methyl-N-phenylcarbamoylmethyl) dithiocarbonate and hydrazine hydrate are used as starting substances, the course of the reaction in process (a) according to the invention can be represented by the following equation:

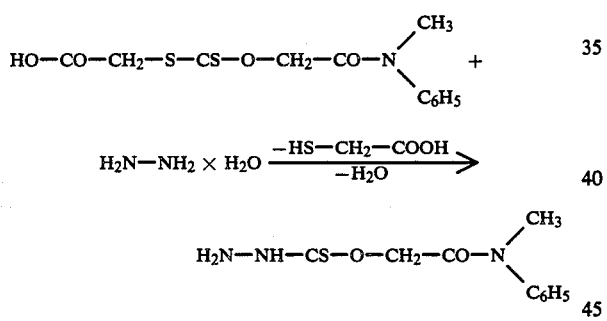

If, for example, hydroxyacetic acid piperidide, carbon disulphide, potassium hydroxide, sodium chloroacetate and hydrazine hydrate are used as the starting substances, the course of the reaction in process (b) according to the invention can be represented by the following equation:

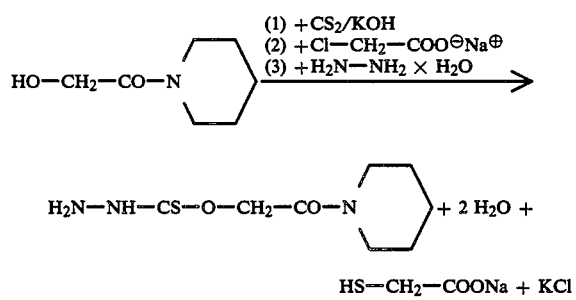

Formula (II) provides a general definition of the O-carbamoylmethyl S-carboxymethyl dithiocarbonates required as starting substances for carrying out process (a) according to the invention. In this formula (II) R¹ and R² preferably represent those radicals which have already been mentioned as preferred for these substituents in the description of the substances of the formula (I) according to the invention.

The O-carbamoylmethyl S-carboxymethyl dithiocarbonates of the formula (II) are not yet known. They are obtained by a process in which hydroxyacetamides of the formula (III)

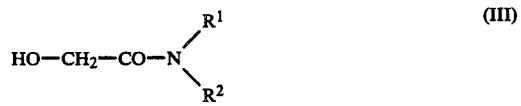

in which
R¹ and R² have the abovementioned meaning,
are reacted successively in a "one-pot process", first with carbon disulphide in the presence of a base, such as, for example, an alkali metal hydroxide, and then with an alkali metal chloroacetate, such as, for example, sodium chloroacetate, and finally with an acid, such as, for example, hydrochloric acid, if appropriate in the presence of a diluent, such as, for example, water, at temperatures between 0° C. and +60° C.

This invention likewise relates to the new O-carbamoyl S-carboxymethyl dithiocarbonates (II) and the process described above for their preparation.

Formula (III) provides a general definition of the hydroxyacetamides required as starting substances for carrying out process (b) according to the invention and for the synthesis of the precursors of the formula (II). In this formula (III), R¹ and R² preferably represent those radicals which have already been mentioned as preferred for these substituents in the description of the substances of the formula (I) according to the invention.

The hydroxyacetamides of the formula (III) are known (compare, for example, European Pat. No. 18,497, European Pat. No. 29,171, DE-OS (German Published Specification) No. 3,038,598 and DE-OS No. 3,148,839).

Possible diluents for carrying out process (a) according to the invention are organic solvents or aqueous systems.

Water-miscible solvents, such as, for example, methanol, ethanol or acetonitrile, or mixtures thereof with water, are preferably used. The use of pure water as the diluent is particularly preferred.

Possible acid-binding agents in carrying out process (a) according to the invention are in principle all the inorganic or organic bases which can customarily be used. Bases which are preferably used are alkaline earth metal carbonates or bicarbonates or alkali metal carbonates or bicarbonates, such as, for example, sodium bicarbonate or potassium bicarbonate.

The reaction temperatures can be varied within a substantial range in carrying out process (a) according to the invention. In general, the reaction is carried out at temperatures between $-20°$ C. and $+50°$ C., preferably between $0°$ C. and $+30°$ C.

For carrying out process (a) according to the invention, in general 1 to 1.3 moles, preferably equimolar amounts of hydrazine hydrate and in general 1 to 1.3, preferably 1 to 1.1, moles of acid-binding agent are employed per mole of O-carbamoylmethyl S-carboxymethyl dithiocarbonate of the formula (II).

For working up, any acid-binding agent still present in excess is neutralized and the reaction product of the formula (I), which is insoluble in water, is isolated by filtration.

Possible diluents for carrying out process (b) according to the invention are likewise water-miscible inert organic diluents or aqueous systems. Pure water is preferably used as the diluent.

Possible bases in carrying out process (b) according to the invention are strong inorganic bases. Bases which are preferably used are alkali metal hydroxides, such as, for example, sodium hydroxide or potassium hydroxide.

The reaction temperature can likewise be varied within a substantial range in carrying out process (b) according to the invention. In general, the reaction is carried out at temperatures between $-20°$ C. and $+60°$ C., preferably between $0°$ C. and $+40°$ C.

For carrying out process (b) according to the invention, in general 1 to 1.3 moles of carbon disulphide, 1 to 1.3 moles of alkali metal chloroacetate, such as, for example, sodium chloroacetate, 1 to 1.3 moles of hydrazine hydrate and 1 to 1.3 moles of base are employed per mole of hydroxyacetamide of the formula (III), and equimolar amounts of all the required reactants are preferably used. Working-up and isolation of the reaction products of the formula (I) are effected in the customary manner.

As already mentioned, the hydrazine-thiocarboxylic acid O-carbamoylmethyl esters of the formula (I) according to the invention are useful intermediates.

They can easily be converted into 1,3,4-thiadiazol-2-yloxyacetamides of the general formula (IV)

$$\underset{R^3}{\overset{N\text{———}N}{\underset{S}{\parallel}\phantom{xx}\underset{}{\parallel}}}\text{O—CH}_2\text{—CO—N}\overset{R^1}{\underset{R^2}{}} \quad (IV)$$

in which $R^1$ and $R^2$ have the abovementioned meanings and
$R^3$ represents alkyl, halogenoalkyl, aralkyl or optionally substituted aryl, by a process in which the compounds of the formula (I) are reacted with generally known carboxylic acid anhydrides of the formula (V)

$$R^3\text{—CO—O—CO—R}^3 \quad (V)$$

in which $R^3$ has the abovementioned meaning, if appropriate in the presence of a diluent, such as, for example, methylene chloride, at temperatures between $-30°$ C. and $+30°$ C.

The 1,3,4-thiadiazol-1-yloxyacetamides of the formula (IV) have herbicidal properties (compare, for example, DE-OS (German Published Specification) No. 2,914,003, DE-OS No. 3,004,326, European Pat. No. 18,497, DE-OS No. 2,946,526, European Pat. No. 29,171 and DE-OS No. 3,218,482).

PREPARATION EXAMPLES

Example 1

$$\text{H}_2\text{N—NH—CS—O—CH}_2\text{—CO—N}\overset{CH_3}{\underset{C_6H_5}{}}$$

(Process a)

29.9 g (0.1 mole) of S-carboxymethyl O-(N-methyl-N-phenylcarbamoylmethyl)dithiocarbonate are added in portions to a solution of 9.3 g (0.11 mole) of sodium bicaronate in 100 ml of water. After 1 hour, 5 g (0.1 mole) of hydrazine hydrate are added dropwise at $5°$ C. to $10°$ C., the mixture is subsequently stirred for 1 hour, with cooling, and the product which has precipitated is then filtered off with suction.

20 g (84% of theory) of O-(N-methyl-N-phenylcarbamoylmethyl)hydrazine-thiocarboxylate are obtained in this manner in the form of a beige powder of melting point $104°$ C.

(Process b)

33 g (0.2 mole) of glycolic acid N-methylanilide are first added to a solution of 11.2 g (0.2 mole) of potassium hydroxide in 40 ml of water at $10°$ C., followed by 15.2 g (0.2 mole) of carbon disulphide. The mixture is subsequently stirred at $10°$ C. to $15°$ C. for 10 minutes and 23.2 g (0.2 mole) of sodium chloroacetate are added to the suspensions thereby formed. The temperature of the reaction mixture rises to about $38°$ C. After 1 hour, 10 g (0.2 mole) of hydrazine hydrate are added dropwise at $5°$ C. to $10°$ C., with cooling, 100 ml of ice-water are added to the mixture and the mixture is extracted 3 times with 50 ml of chloroform each time.

After the solvent has been evaporated off, 43.2 g (90% of theory) of O-(N-methyl-N-phenylcarbamoylmethyl)hydrazine-thiocarboxylate are obtained in the form of light gray crystals of melting point $113°$ C.

The following compounds of the general formula (I) are obtained in a corresponding manner and in accordance with the general preparation instructions:

TABLE 2

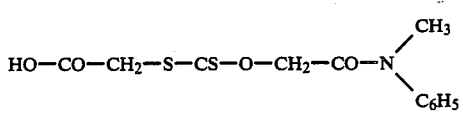

| Example No. | R¹ | R² | Physical properties |
|---|---|---|---|
| 2 | $CH_3-(CH_2)_2-$ | $CH_3-(CH_2)_2-$ | $n_D^{22}$ 1.5274 |
| 3 | $-CH-CH_2-CH_2-CH_2-CH_2-$<br>$\ \ \ \ \|$<br>$\ \ \ C_2H_5$ | | $n_D^{22}$ 1.5445 |
| 4 | $C_2H_5$ | $C_2H_5$ | $n_D^{22}$ 1.5440 |
| 5 | $CH_2=CH-CH_2-$ | $CH_2=CH-CH_2-$ | $n_D^{24}$ 1.5543 |

PREPARATION OF THE STARTING COMPOUNDS

Example II-1

$$HO-CO-CH_2-S-CS-O-CH_2-CO-N\begin{smallmatrix}CH_3\\ \\C_6H_5\end{smallmatrix}$$

16.5 g (0.1 mole) of glycolic acid N-methylanilide are first added to a solution of 5.6 g (0.1 mole) of potassium hydroxide in 20 ml of water, followed by 7.6 g (0.1 mole) of carbon disulphide. The mixture is subsequently stirred at 10° C. to 15° C. for 10 minutes and 11.6 g (0.1 mole) of sodium chloroacetate are then added. The temperature thereby rises up to about 32° C. After 1.5 hours, the mixture is diluted with 40 ml of water and brought to pH 2 with concentrated hydrochloric acid. The product which has precipitated is shaken twice with 100 ml of methylene chloride each time and the organic phase is dried over sodium sulphate and evaporated in vacuo.

27.8 g (93% of theory) of S-carboxymethyl O-(N-methyl-N-phenylcarbamoylmethyl)dithiocarbonate are obtained in the form of yellow crystals of melting point 109° C.

The following precursors of the general formula (II) are obtained in a corresponding manner:

TABLE 3

$$HO-CO-CH_2-S-CS-O-CH_2-CO-N\begin{smallmatrix}R^1\\ \\R^2\end{smallmatrix} \quad (II)$$

| Example No. | R¹ | R² | Physical properties |
|---|---|---|---|
| II-2 | $CH_3-(CH_2)_2-$ | $CH_3-(CH_2)_2-$ | Melting point 96° C. |
| II-3 | $-CH-CH_2-CH_2-CH_2-CH_2-$<br>$\ \ \ \ \|$<br>$\ \ \ C_2H_5$ | | $n_D^{27}$ 1.5411 |
| II-4 | $C_2H_5$ | $C_2H_5$ | Melting point 122° C. |
| II-5 | $CH_2=CH-CH_2-$ | $CH_2=CH-CH_2-$ | Melting point 108° C. |

USE EXAMPLES
(Preparation of the secondary products)

Example IV-1

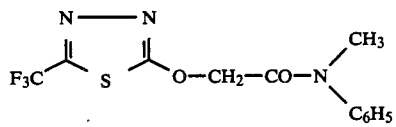

30.3 g (0.144 mole) of trifluoroacetic anhydride are added to a mixture of 14.4 g (0.06 mole) of O-(N-methyl-N-phenylcarbamoylmethyl)hydrazine-thiocarboxylate and 60 ml of methylene chloride at 0° C. to 5° C. and the mixture is subsequently stirred at room temperature for 18 hours. It is then extracted by shaking with water and saturated sodium bicarbonate solution, the organic phase is dried over sodium sulphate and the solvent is distilled off in vacuo.

18.1 g (95% of theory) of (5-trifluoromethyl-1,3,4-thiadiazol-2-yl)-oxyacetic acid N-methylanilide are obtained in the form of a colorless powder of melting point 58° C.

The following herbicidal 1,3,4-thiadiazol-2-yl-oxyacetamides of the general formula (IV) are obtained in a corresponding manner:

TABLE 4

$$\underset{R^3}{}\overset{N-N}{\underset{S}{\diagup\!\!\diagdown}}-O-CH_2-CO-N\begin{smallmatrix}R^1\\ \\R^2\end{smallmatrix} \quad (IV)$$

| Example No. | R¹ | R² | R³ | Physical properties |
|---|---|---|---|---|
| IV-2 | $CH_3-(CH_2)_2-$ | $CH_3-(CH_2)_2-$ | $CF_3$ | $n_D^{21}$ 1.4558 |
| IV-3 | $-CH-CH_2-CH_2-CH_2-CH_2-$<br>$\ \ \ \ \|$<br>$\ \ \ C_2H_5$ | | $CF_3$ | $n_D^{22}$ 1.4883 |
| IV-4 | $C_2H_5$ | $C_2H_5$ | $CF_3$ | $n_D^{21}$ 1.4688 |
| IV-5 | $CH_2=CH-CH_2-$ | $CH_2=CH-CH_2-$ | $CF_3$ | $n_D^{22}$ 1.4800 |

It will be understood that the specification and examples are illustrative but not limitative of the present invention and that other embodiments within the spirit and scope of the invention will suggest themselves to those skilled in the art.

I claim:
1. An ester of the formula

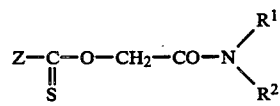

in which
Z is $H_2N-NH-$ and
R¹ and R² each independently is hydrogen, alkyl, alkenyl or alkynyl with up to 8 carbon atoms, cycloalkyl or cycloalkenyl each of which has 3 to 7 carbon atoms and is optionally substituted by alkyl with 1 to 4 carbon atoms, alkoxy or alkoxyalkyl with 1 to 8 carbon atoms, halogenoalkyl with 1 to 8 carbon atoms and 1 to 5 halogen atoms, aralkyl with 6 to 10 carbon atoms in the aryl part and 1 or 2 carbon atoms in the alkyl part, or aryl which has 6 to 10 carbon atoms and is optionally substituted by halogen, alkyl, alkoxy or alkylthio with in each case 1 to 4 carbon atoms, halogenoalkyl, halogenoalkoxy or halogenoalkylthio with in each case 1 or 2 carbon atoms and 1 to 5 halogen atoms, or nitro; or $R^1$ and $R^2$, together with the nitrogen atom to which they are bonded, form a 5-membered to 7-membered heterocyclic radical which can contain up to 2 further hetero-atoms nitrogen and/or oxygen atoms, and which is optionally substituted by alkyl with 1 to 6 carbon atoms, also in the form of a fused-on ring system, aryl with 6 to 10 carbon atoms, also in the form of a fused-on ring system, or dioxyalkylene with 2 or 3 carbon atoms.

2. An ester according to claim 1, in which $R^1$ and $R^2$ each independently is hydrogen, alkyl, alkenyl or alkinyl with in each case up to 6 carbon atoms, cycloalkyl or cycloalkenyl each of which has 5 to 7 carbon atoms and is optionally mono-, di- or tri-substituted by methyl, ethyl, alkoxy or alkoxyalkyl with 1 to 6 carbon atoms, halogenoalkyl with 1 to 6 carbon atoms and 1 to 5 halogen atoms, benzyl, or phenyl which is optionally mono-, di- or tri-substituted by methyl, ethyl, methoxy, methylthio, trifluoromethyl, trifluoromethoxy, trifluoromethylthio, fluoro, chloro or nitro; or $R^1$ and $R^2$, together with the nitrogen atom to which they are bonded, form

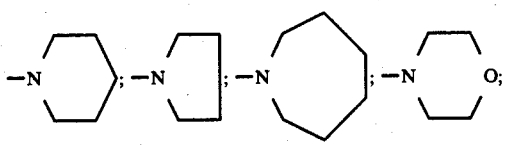

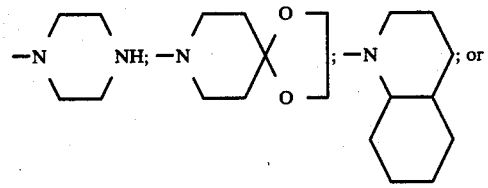

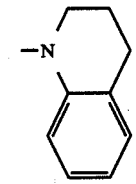

each optionally substituted up to three times by methyl, ethyl or phenyl.

* * * * *